United States Patent
Schoenefeld (10) Patent No.: US 6,827,722 B1
(45) Date of Patent: Dec. 7, 2004

(54) METHOD AND APPARATUS FOR USE OF A GUIDE WIRE CAPTURING SURGICAL INSTRUMENT

(75) Inventor: Ryan J. Schoenefeld, Fort Wayne, IN (US)

(73) Assignee: Biomet, Inc., Warsaw, IN (US)

( * ) Notice: Subject to any disclaimer, the term of this patent is extended or adjusted under 35 U.S.C. 154(b) by 352 days.

(21) Appl. No.: 10/014,671

(22) Filed: Dec. 11, 2001

(51) Int. Cl.[7] .............................................. A61B 17/56
(52) U.S. Cl. ........................... 606/104; 606/73; 606/88
(58) Field of Search .................... 606/99, 104, 232, 606/103, 72–73, 59; 81/436, 442, 480; 600/104, 585

(56) References Cited

U.S. PATENT DOCUMENTS

| | | | | |
|---|---|---|---|---|
| 2,248,054 A | * | 7/1941 | Becker ........................ | 81/457 |
| 4,124,026 A | * | 11/1978 | Berner et al. ................ | 606/104 |
| 4,587,963 A | * | 5/1986 | Leibinger et al. ........... | 606/103 |
| 5,071,420 A | * | 12/1991 | Paulos et al. ................ | 606/99 |
| 5,203,784 A | * | 4/1993 | Ross et al. ................... | 606/104 |
| 5,257,996 A | | 11/1993 | McGuire | |
| 5,323,765 A | | 6/1994 | Brown | |
| 5,391,170 A | | 2/1995 | McGuire et al. | |
| 5,423,819 A | * | 6/1995 | Small et al. .................. | 606/73 |
| 5,464,407 A | | 11/1995 | McGuire | |
| 5,520,693 A | | 5/1996 | McGuire et al. | |
| 5,658,289 A | | 8/1997 | Boucher et al. | |
| 6,436,100 B1 | * | 8/2002 | Berger ......................... | 606/73 |

* cited by examiner

Primary Examiner—David O. Reip
Assistant Examiner—D. Jacob Davis
(74) Attorney, Agent, or Firm—Harness, Dickey & Pierce, P.L.C.

(57) ABSTRACT

Disclosed is a driven surgical driver for wire guide surgical components. The driver has a rotatable drive shaft which is configured to apply driving and rotational forces to a medical device. A wire clamp is provided which is configured to hold the guide wire at a fixed distance from the tissue while the medical device is being driven distally away from the wire clamp. A process provides for grasping a point on the guide wire at a fixed distance from the tissue with the wire clamp. This grasping point on the guide wire is maintained at the fixed distance from the tissue while a force is applied to the driver to affix the medical device relative to the tissue.

14 Claims, 6 Drawing Sheets

METHOD AND APPARATUS FOR USE OF A GUIDE WIRE CAPTURING SURGICAL INSTRUMENT

TECHNICAL FIELD

The present invention pertains generally to a guide wire capturing surgical instrument and, more particularly, to a cannulated guide wire surgical instrument used for driving bone screws, resurfacing and drilling instruments or other surgical devices.

BACKGROUND OF THE INVENTION

The use of orthopedic fastening devices, such as bone screws, has greatly aided the medical field in the treatment of bone fractures, as well as enabling the ever increasing use of orthopedic implants and orthopedic appliances. With respect to the treatment of bone fractures, it is sometimes generally necessary to surgically reposition the fragmented bone members in an atomically acceptable orientation, and then fasten the bone members together in order to facilitate the healing process. Bone screws are typically employed in stabilization procedures used to treat bone fractures.

When a bone screw is employed, either to fasten two or more members together or to secure an orthopedic appliance (e.g. bone plate) to a bone, alignment and proper orientation is critical. To ensure proper alignment, a guide wire is often installed along the desired trajectory for the bone screw. The cannulated bone screw is then disposed over the guide wire. The guide wire functions to guide the cannulated bone screw in its proper direction. After the insertion of the bone screw, the guide wire is removed from the joined components.

Typically, a cannulated drive is used to drive the cannulated screw over the guide wire. After the cannulated screw has been deposited over the guide wire, the guide wire is typically threaded through a cannulated driver. As the driver rotates the screw, it is intended that the guide wire will rotate within the driver. Unfortunately, occasionally the guide wire will get caught or hung up on the driven screw. As a result, the wire which has been deposited through the cannulated screw is likewise rotated, thus allowing the guide wire to further insert itself into the patient. This creates a situation where it is possible that the moving guide wire could pierce some part of the patient, resulting in unnecessary pain or soft tissue damage.

Other uses of guide wires are also known for other surgical procedures. For example, natural joints may undergo degenerative changes due to a variety of etiologies. When these degenerative changes become so far advanced and irreversible, it may ultimately become necessary to replace a natural joint with a prosthetic joint. During the orthopedic procedure, it is generally known in the art to prepare either side of the joints natural material using guide wire guided cutting devices such cannulated drill bits and driven cannulated reamers. However, here again, the current prior art cannulated drill bits and reamers and associated surgical components may suffer from many disadvantages associated with the inadvertent driving of the guide wire as discussed above. What is needed then is a capturing guide wire surgical instrument that does not suffer from the above-mentioned disadvantages.

SUMMARY OF THE INVENTION

The present invention provides in one embodiment a driven surgical driver for driving a cannulated bone screw into the bone. This screw is disposed over a guide wire. The driven surgical driver is cannulated and is coupled to a driver which has an actuatable clamp capable of clamping the guide wire to prevent undesirable further insertion of the guide wire into the bone.

In one embodiment, a driven surgical driver is disclosed that has an internal clamp which clamps a guide wire. The wire clamp is configured to hold the guide wire a fixed distance from the tissue while a medical device is driven distally away from the wire clamp by a driven shaft.

In another embodiment, an apparatus for driving a medical device having a guide wire clasping driven member which maintains the length of a guide wire coupled to a tissue. The apparatus for driving a medical device has a rotatable shaft configured to be coupled to the medical device and a wire clamp which clamps the wire at a fixed distance from the tissue. A driver is coupled to the rotatable drive shaft.

In another embodiment of the invention, a driven member is provided. The driven member has a proximal end which is configured to drive a fastener. On its proximal end, the member has a quick connect member which allows the driven member to be quickly coupled to a driver. Disposed between the proximal and distal ends is a clamp which is configured to fixedly couple a surgical guide wire.

Further disclosed is a method for rotating a medical device with respect to a biological tissue having a guide wire. The method includes providing a medical device and a guide wire clasping member having a driven shaft and a wire clamp. The wire clamp is configured to hold the guide wire at a fixed distance from the tissue. The method further includes positioning the guide wire clamping member relative to the medical device, and clamping the guide wire at a fixed distance from the tissue. Forces are applied to the draft shaft which applies forces to the medical device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses. Moreover, while the present invention is discussed below in relation to driving a bone screw, those skilled in the art will recognize that the cannulated segmented devices such as drills and reamers may be used.

Figure 1:
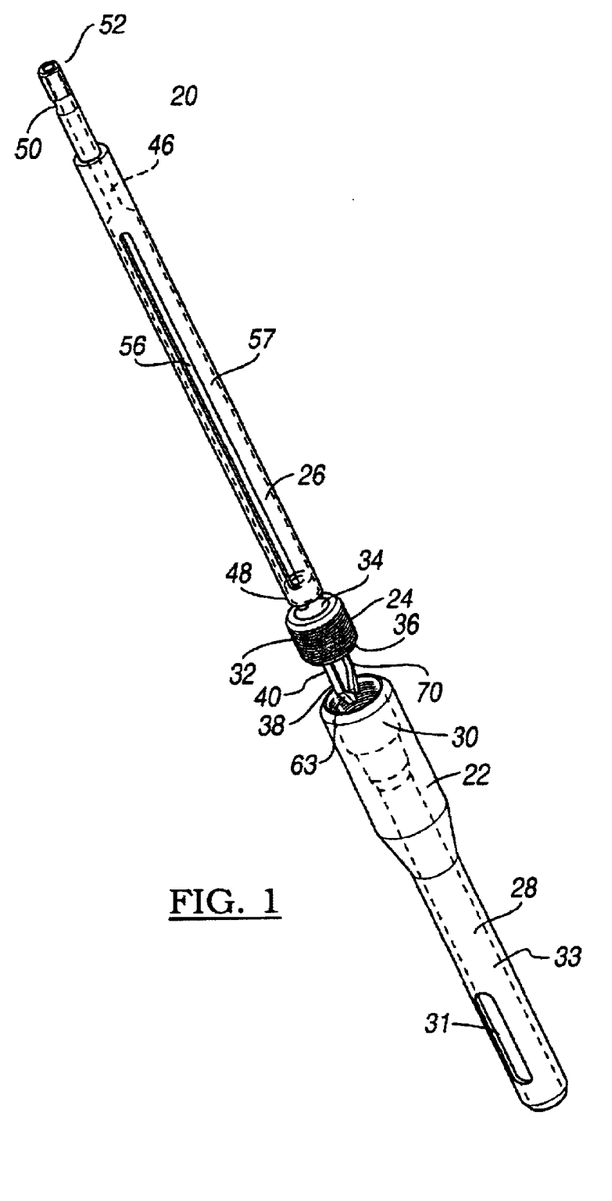
FIG. 1 is a exploded perspective view of a wire capturing driver of a first embodiment of the present invention.
Figure 2:
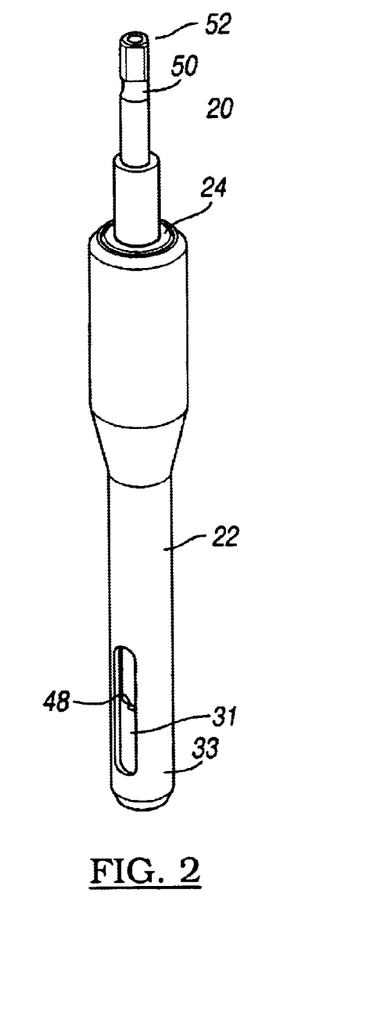
FIG. 2 is an assembled view of the wire capturing driver shown in FIG. 1.

FIGS. 1 and 2 depict a perspective view of a driven member 20 according to a first embodiment of the present invention. The driven member 20 is formed generally of three components, an outer sleeve 22, a wire fastener or retaining member 24 and a central shaft 26.

The outer sleeve 22 defines a first central through bore 28 which slidably accepts the central shaft 26. The outer sleeve 22 defines an axial threaded bore 30 which accepts a threaded exterior surface 32 on the wire fastener 24. The outer sleeve 22 further defines a slot 31 disposed on an exterior surface 33. The slot 31 assists in the proper orientation of a fastener with the driver member 20, further discussed herein.

The wire fastener 24 is an annular member which defines a through bore 34. The through bore 34 is configured to slidably accept the central shaft 26. Disposed on the proximal surface 36 of the wire fastener 24 is a pair of wire clasping jaws 38 (see FIG. 3a). The wire clasping jaws 38 are coupled to the proximal surface 36 by a pair of generally parallel flanges 40. The flanges 40 are configured to deformably or resiliently allow the wire clasping jaws 38 to move from a first non-engaged position 42 to an engaged position 44 (see FIGS. 3a and 3c).

As best shown in FIG. 1, the central shaft 26 defines a guide wire accepting through bore 46. The proximal end 48 of the central shaft 26 defines a cannulated screw engaging portion. Alternatively, the proximal end 48 can define a quick coupler which allows for varying styles of fastener driving heads to be coupled to the central shaft 26. Examples of these include Phillips, straight, or star heads.

The distal end 52 of the central shaft 26 defines a cannulated quick coupling member 50. The quick coupling member 50 facilitates the coupling of the driven member 20 with a driver (not shown). It is envisioned that the driver can be a standard screw driver handle, an electric or pneumatic powered driver such as a drill, or any other type of driver. Disposed between the proximal and distal ends 48 and 52 is a pair of slots 56 defined on an exterior surface 57 of the central shaft 26. The slots 56 are configured to slidably accept the pair of wire capturing jaws 38 of the wire fastener 24.

Figure 3A:
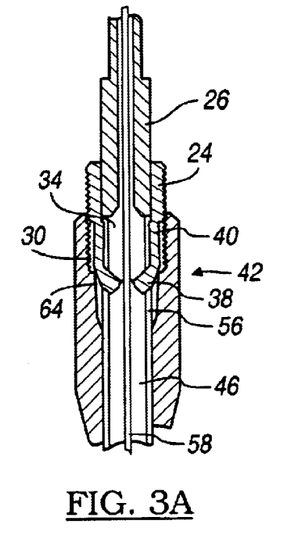
FIGS. 3a–3c are cross-sectional views of the wire capturing driver of the present invention.
Figure 3B:
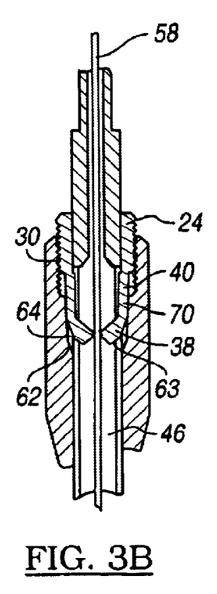
Figure 3C:
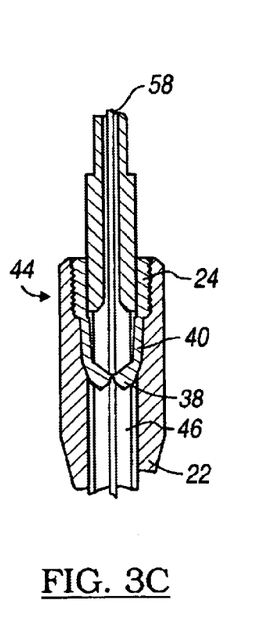

As best shown in FIGS. 3a–3c, the central shaft 26 is disposed within the through bore 34 of the wire fastener 24 such that the wire clasping jaws 38 are disposed through the slots 56 into the wire accepting through bore 46. As can be seen, the central shaft 26 is slidable within both the wire fastener 24 and the first through bore 28 of the outer sleeve 22.

The guide wire 58 is threaded through an aperture 60 in the proximal end 48 of the central shaft 26 into the wire accepting through bore 46. The guide wire 58 is then threaded between the wire clasping jaws 38. The threaded exterior surface 32 of the wire fastener 24 is then inserted into the axially threaded bore 30 of the outer sleeve 22. Further defined within the outer sleeve 22 is an angled shoulder 62 which functions to engage an angled surface 63 on the wire clasping jaws 38. As the wire fastener 24 is rotatably inserted into the axially threaded bore 30, the angled shoulder 62 engages the angled surface 63 of the wire clasping jaws 38. As the wire fastener 24 is inserted further, the angled surface 63 functions to force the wire clasping jaws 38 together and engage them with the guide wire 58. It does so by bending or flexing of the flanges 40.

Figure 4:
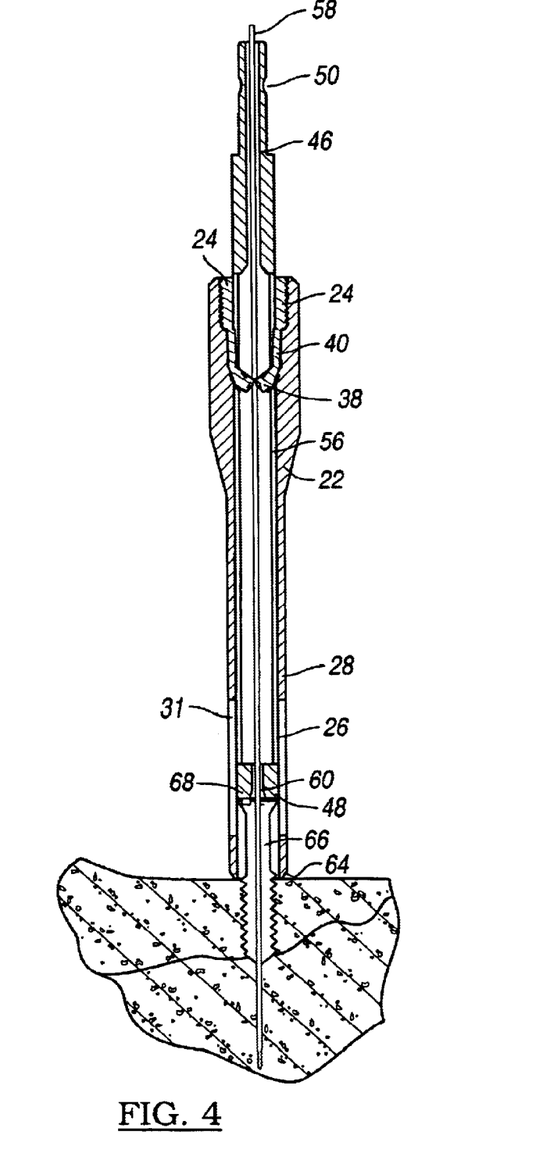
FIG. 4 is a cross-sectional view the wire capturing driver of the present invention driving a cannulated bone screw.

FIG. 4 depicts a cross-sectional view of the driven member 20 of the first embodiment of the invention engaging a cannulated bone fastener or screw 66. The drive member 20 is shown with the guide wire 58 clasped between the wire clasping jaws 38. The proximal end 64 of the outer sleeve 22 is shown engaged with the surface of the bone being joined. As can be seen, the cannulated bone fastener 66 is shown disposed within the central through bore 28 of the outer sleeve 22 and engaged with the driver head 68 found on the proximal end 48 of the central shaft 26. The driver head 68 may be of any shape including Phillips, hex, regular, etc.

When the central shaft 26 is rotated by a driver (not shown), the driver head 68 rotates the cannulated bone fastener 66 into the bone. The rotation of the central shaft 26 also rotates the outer sleeve 22. Rotational forces from the central shaft 26 are transmitted to the outer sleeve 22 through the side surfaces 70 of the wire clasping jaws 38. Because the guide wire 58 is fixed with respect to the outer sleeve 22 and the central shaft 26 is slidable within the outer sleeve 22, the cannulated bone fastener 66 can be driven while the depth of the threaded guide wire 58 is held in a substantially predetermined and fixed position. The wire clasping jaws 38 can be disengaged from the guide wire 58 by lifting the driver head 68 off the cannulated bone fastener 66, holding the outer sleeve 22 to prevent its rotation, and rotating the central shaft 26 in a reverse direction.

While the figures show the use of the driven member 20 to drive a cannulated bone screw, it should be understood that the driven member is equally usable for use with tissue cutting devices such as drill bits and reamers. Furthermore, while the components are depicted as being coaxial, there is no requirement that the wire clamp be coaxial with the driven shaft or the driver or that the driven member be cannulated.

Figures 5, 6:
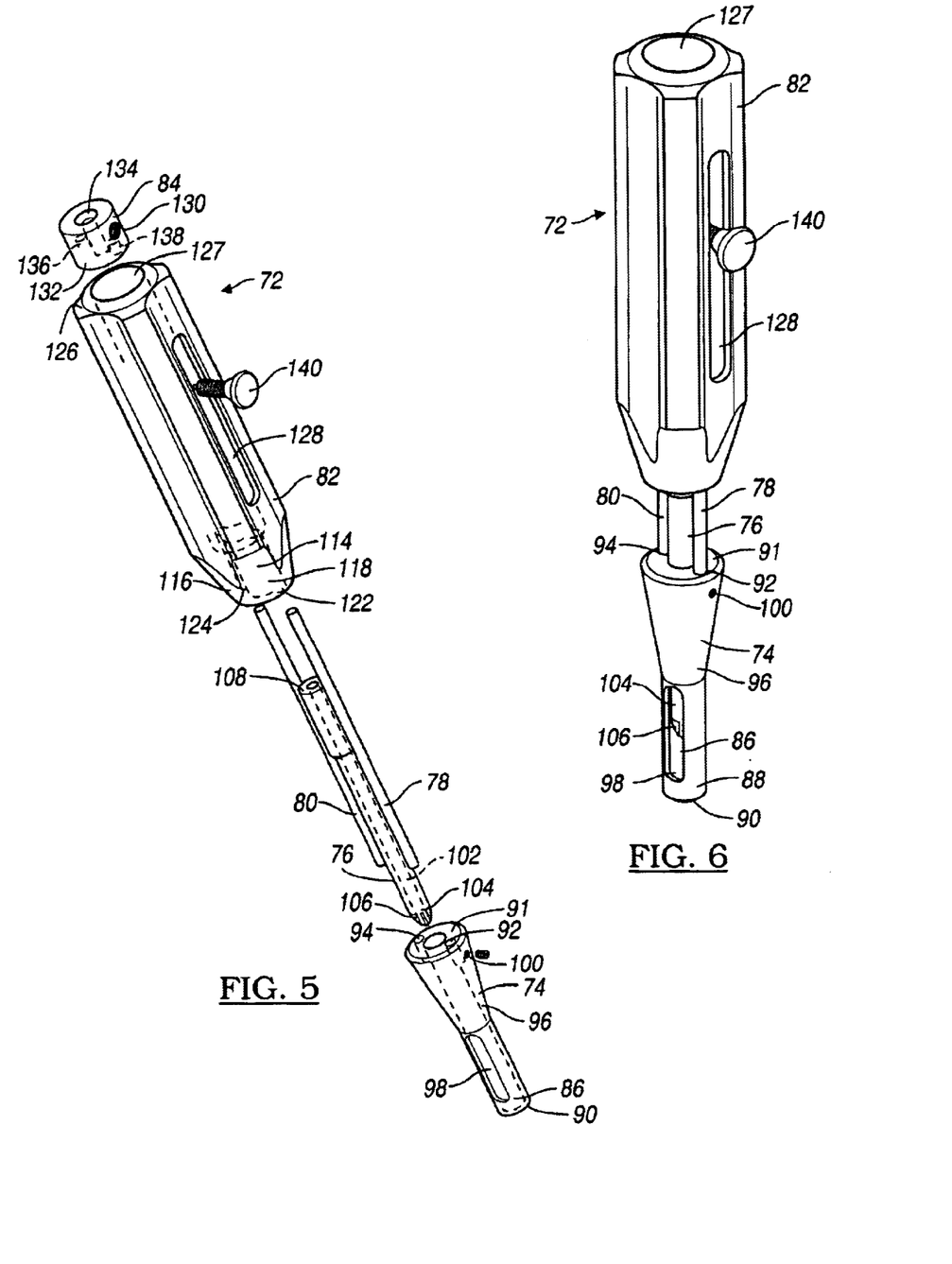
FIG. 5 is an exploded view of a second embodiment of the present invention.
FIG. 6 is an assembled view of the second embodiment of the present invention.

With reference to FIGS. 5 and 6 which depict a fastener driver 72 according to a second preferred embodiment of the invention, shown is an outer sleeve 74, a central shaft 76, spacer bars 78 and 80, a handle 82, and a wire locking member or mechanism 84.

The outer sleeve 74 defines a first axial through bore 86. The proximal end 88 of the outer sleeve 74 defines a bone engaging surface 90, and the distal end 91 of the outer sleeve 74 defines a pair of apertures 92 and 94 which engage the spacer bars 78 and 80. Defined within the exterior surface 96 of the outer sleeve 74 is shown at least one slot 98 and a pair of through threaded holes 100 which define a bore into the pair of apertures 92 and 94. The slot 98 allows the surgeon to ensure the control shaft 76 is properly seated prior to locking the guide wire 58 (as further described below).

The central shaft 76 is a cannulated rod which defines an interior guide wire accepting bore 102. The central shaft proximal end 104 defines either a cannulated screw engaging member 106 or a quick coupler (not shown) which will accept a cannulated screw engaging member 106.

The handle 82 defines an axial through bore 114. Disposed on the proximal end 116 of the handle 82 is a first aperture 118. The first aperture 118 accepts the distal end 108 of the central shaft 76. The proximal end 116 of the handle 82 further defines a pair of holes 122 and 124 which slidably accept the spacer bars 78 and 80.

Defined within the distal end 126 of the handle 82 is a bore 127. The bore 127 is configured to slidably accept the wire locking member 84. Disposed between the proximal and distal ends 116 and 126 is a through slot 128. The through slot 128 allows access to a threaded through bore 130 formed in an exterior surface 132 of the wire locking member 84.

The wire locking member 84 is an annular member defining three bores therethrough. The first axial bore 134 is configured to accept the guide wire 58. A pair of through bores 136 and 138 are configured to slidably accept the spacer bars 78 and 80. The threaded through bore 130 is configured to accept a threaded knob 140. The threaded knob 140 is configured to clamp the guide wire 58 within the first axial bore 134.

Figure 7A:
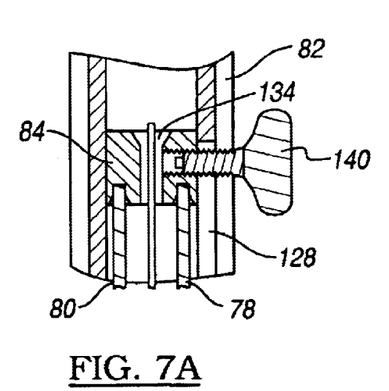
FIGS. 7a–7b represent cross-sectional view of a coupling mechanism of the second embodiment of the present invention.
Figure 7B:
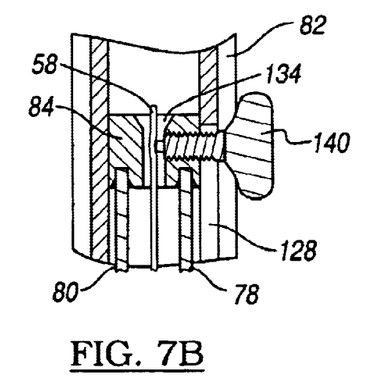

As is shown in FIGS. 7a–7b, the guide wire 58 is disposed through the first axial bore 134 of the wire locking member 84. The threaded knob 140 is disposed through the slot 128 of handle 82 and functions to clamp the guide wire 58 within the first axial bore 134. The threaded knob 140 is further configured to allow the handle 82 to slide with relationship to the wire locking member 84.

Figure 8:
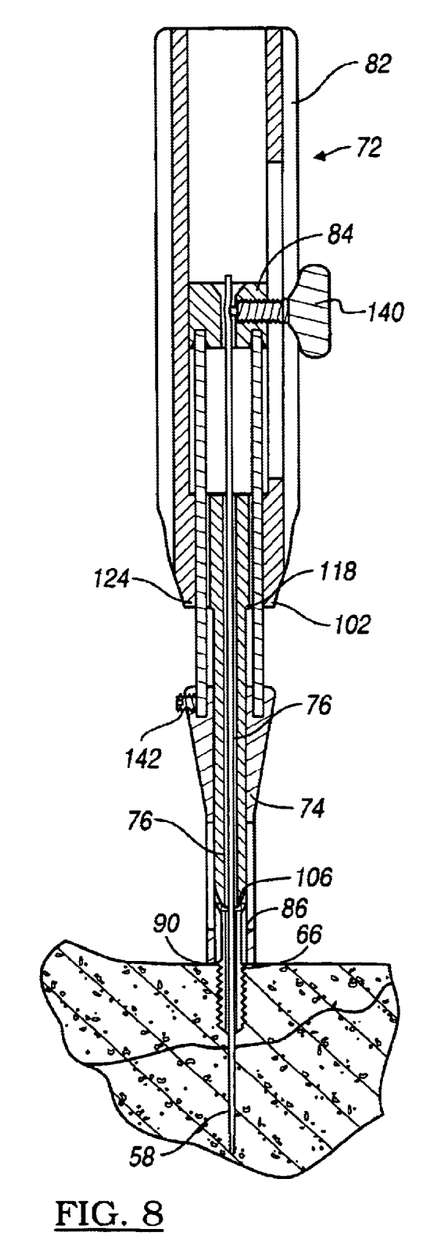
FIG. 8 is a cross-sectional view of the second embodiment of the present invention driving a cannulated screw into bone material.

FIG. 8 is a cross-sectional view of the fastener driver 72 according to the second embodiment of the present invention engaging the cannulated bone fastener 66. The fastener driver 72 is shown with the guide wire 58 clasped within the wire locking member 84. The bone engaging surface 90 of the outer sleeve 74 is shown engaging the bone to be coupled. The cannulated bone fastener 66 is shown disposed within the first axial through bore 86 and engaged with the cannulated screw engaging member 106.

The spacer bars 78 and 80 are shown fixed to the outer sleeve 74 by a set screw 142. One skilled in the art would recognize that spacer bars 78 and 80 can be welded to the outer sleeve 74. The spacer bars 78 and 80 function to fix the distance between the outer sleeve 74 and the locking member 84. The central shaft 76 is operable to slide within the outer sleeve 74 and is fixed to the handle 82. When the central shaft 76 is rotated, the screw engaging member 106 rotates the cannulated bone coupling fastener 66. Rotational forces applied to the handle 82 are also transmitted to the outer sleeve 74. As the central shaft 76 is operable to slide within the outer sleeve 74, the cannulated bone fastener 66 can be driven while the guide wire 58 is prevented from being driven further into the tissue.

Figure 9:
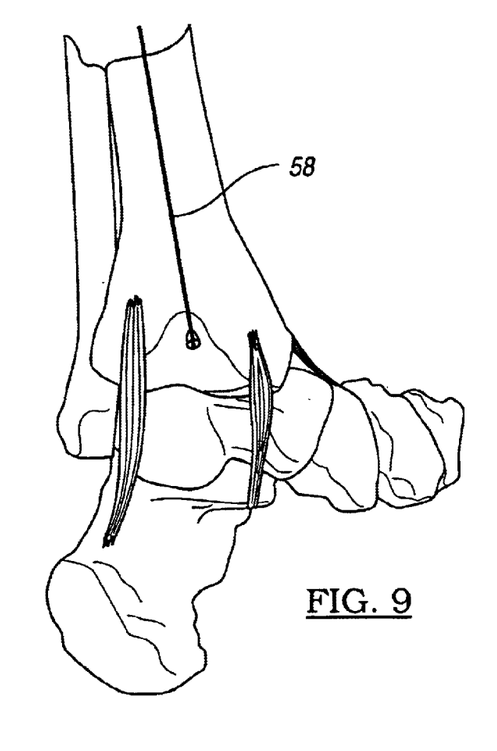
FIGS. 9–12 illustrate a method of using the first embodiment of the present invention to drive a cannulated bone fastener during a surgical procedure.
Figure 10:
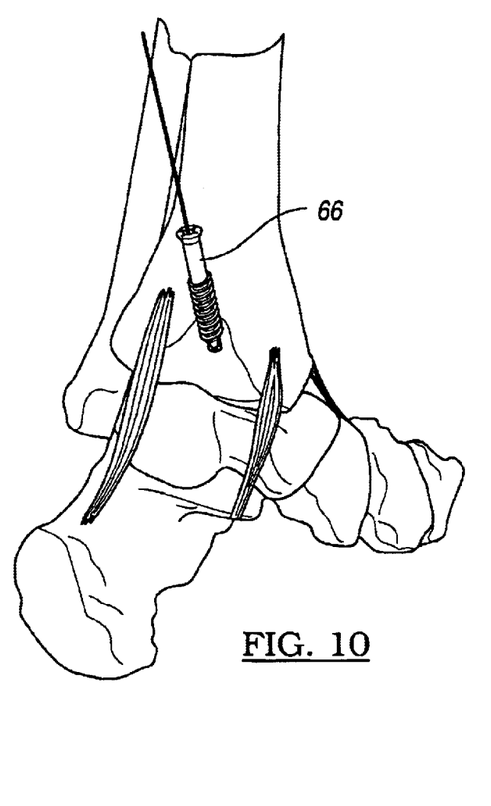

FIGS. 9–12 represent the use of the first and second embodiments of the present invention in a surgical procedure. FIG. 9 shows a guide wire 58 being inserted into the outer maleolas of the tibula as is known in the art. The guide wire 58 will function to provide directional and spatial stability to the cannulated bone fastener 66 while it is being inserted. FIG. 10 depicts the cannulated bone fastener 66 being threaded onto the guide wire 58.

Figure 11:
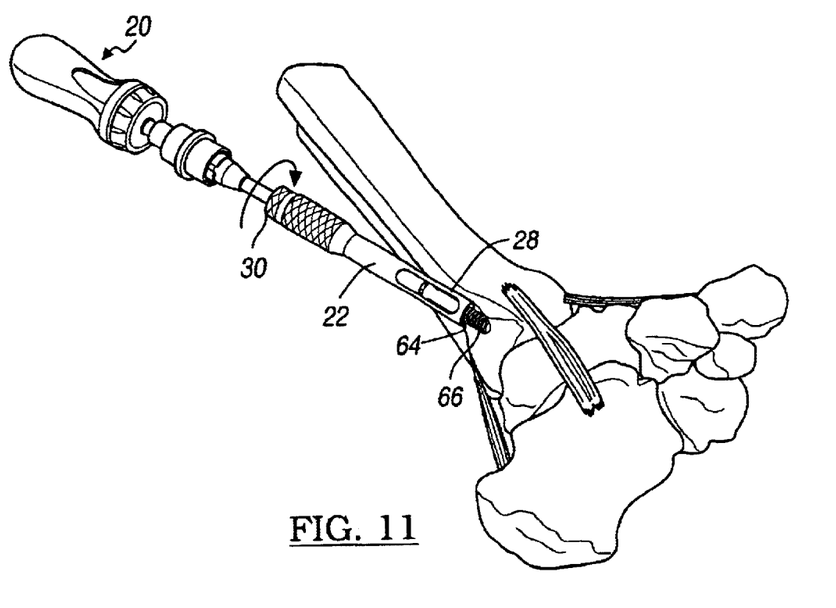

FIG. 11 depicts the use of the first embodiment of the invention. After the cannulated bone fastener 66 is threaded onto the guide wire 58, the guide wire 58 is threaded through the drive member 20. The proximal end 64 of the outer sleeve 22 is seated onto the bone. The cannulated bone fastener 66 is now disposed within the central bore 28 of the outer sleeve 22. The wire fastener 24 is rotated within the axially threaded bore 30, causing the wire clasping jaws 38 to lock onto the guide wire 58. A driver in the form of a handle is used to apply rotational forces to the cannulated bone fastener 66. Once the cannulated bone fastener 66 is inserted, the wire clasping jaws 38 can be disengaged by reverse rotation or the driven member 20 can be used to assist in the removal of the guide wire 58.

Figure 12:
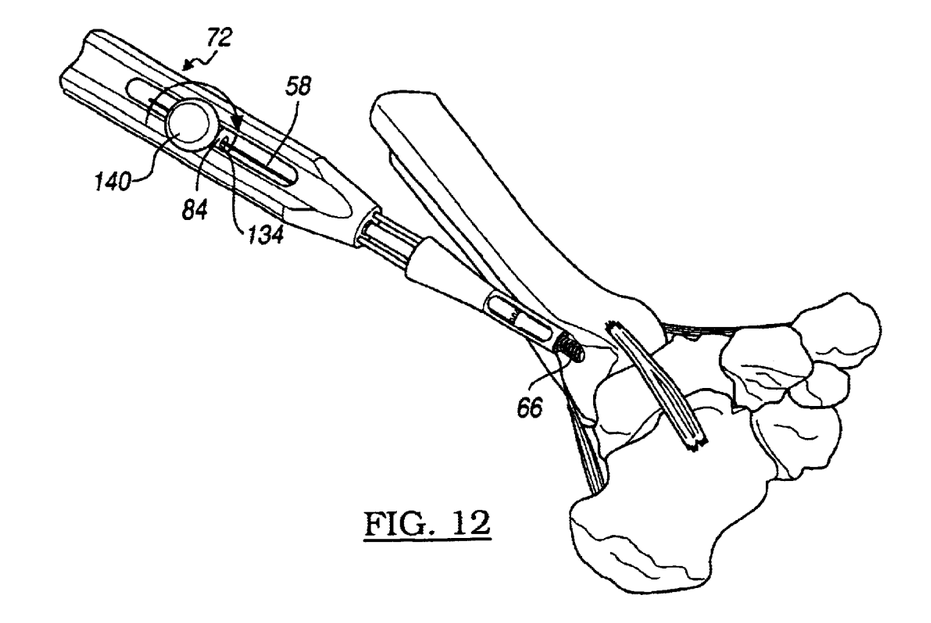

FIG. 12 depicts the use of the second embodiment of the present invention. After the cannulated bone fastener 66 is threaded onto the guide wire 58, the guide wire 58 is threaded through the fastener driver 72. Most importantly, the guide wire 58 is threaded through the wire locking member 84. The bone engaging surface 90 is brought down upon the bone surface, and the threaded knob 140 is rotated to clamp the guide wire 58 within the first axial bore 134. The handle 82 is rotated to cause the cannulated bone fastener 66 to be inserted.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A guide wire clasping driven member which maintains a length of a guide wire disposed in a tissue comprising:
    a rotatable drive shaft configured to apply a driving and rotational force to a medical device; and
    a wire locking mechanism associated with a spacer configured to hold the guide wire a predetermined distance from the tissue as the medical device is driven distally away from the wire locking mechanism.

2. The guide wire clasping driven member according to claim 1 further comprising a cannulated outer sleeve, said rotatable drive shaft being disposed within said cannulated outer sleeve.

3. The guide wire clasping driven member according to claim 2 wherein said outer sleeve is rotatably coupled to said rotatable drive shaft.

4. The guide wire clasping driven member according to claim 2 wherein said wire locking mechanism is disposed within said cannulated sleeve.

5. The guide wire clasping driven member according to claim 1 wherein said wire locking mechanism comprises a threaded knob.

6. The guide wire clasping driven member according to claim 1 wherein the medical device is selected from a group of a fastener, a drill bit, and a cutting tool.

7. The guide wire clasping driven member according to claim 1 wherein the driven shaft is cannulated and configured to accept the guide wire.

8. A guide wire clasping driven member which maintains a length of a guide wire disposed in a tissue comprising:
    a rotatable drive shaft configured to apply a driving and rotational force to a medical device; and
    a wire locking mechanism configured to hold the guide wire a predetermined distance from the tissue as the medical device is driven distally away from the wire locking mechanism, wherein said wire locking mechanism has a pair of guide wire clamping jaws.

9. An apparatus for driving a medical device comprising:
    a guide wire clasping driven member which maintains a length of a guide wire coupled to a tissue comprising a rotatable shaft configured to be coupled to the medical device, and a wire locking mechanism which comprises a pair of collapsible jaws and retains the wire at a predetermined distance from the tissue; and
    a driver coupled to said rotatable drive shaft.

10. A method for rotating a medical device with respect to a biological tissue having a guide wire comprising:

providing a medical device;

providing a guide wire retaining member having a driven shaft and a wire retaining mechanism;

grasping a point on a guide wire at a fixed distance from the biological tissue with the wire retaining mechanism; and applying a force to the driven shaft to affix the medical device with respect to the biological tissue; and maintaining the point on the guide wire at the fixed distance from the biological tissue while applying the force.

11. The method of claim 10 wherein providing a medical device includes providing a medical device selected from a cannulated screw, a cannulated drill bit, and a cannulated cutting tool.

12. The method of claim 10 further comprising placing the guide wire through the medical device.

13. The method of claim 10 wherein providing a guide wire retaining member includes provides a cannulated outer sleeve, said wire retaining mechanism disposed within said outer sleeve.

14. The method according to claim 10 further including providing a driver coupled to the driven shaft, and wherein providing the guide wire retaining member includes providing a wire clamp disposed within the driver.

* * * * *

UNITED STATES PATENT AND TRADEMARK OFFICE
CERTIFICATE OF CORRECTION

PATENT NO. : 6,827,722 B1
DATED : December 7, 2004
INVENTOR(S) : Ryan J. Schoenefeld It is certified that error appears in the above-identified patent and that said Letters Patent is hereby corrected as shown below:

Column 1,
Line 21, "atomically" should be -- anatomically --.
Line 55, "joints" should be -- joint's --.
Line 56, after "such" insert -- as --.

Column 2,
Line 49, "a" should be -- as --.
Line 56, after "view" insert -- of --.
Line 62, "view" should be -- views --.

Column 8,
Line 4, "provides" should be -- providing --.

Signed and Sealed this

Tenth Day of May, 2005

JON W. DUDAS
*Director of the United States Patent and Trademark Office*